United States Patent [19]

McGregor et al.

[11] Patent Number: 4,710,580

[45] Date of Patent: Dec. 1, 1987

[54] 2-[1,3,2-DIOXAPHOSPHOLAN-2-YLOXY]ETHYL COMPOUNDS

[75] Inventors: William H. McGregor, Malvern; Joseph Y. Chang, Berwyn, both of Pa.

[73] Assignee: American Home Products Corporation, New York, N.Y.

[21] Appl. No.: 895,779

[22] Filed: Aug. 12, 1986

[51] Int. Cl.$^4$ .............................................. C07F 9/15
[52] U.S. Cl. .................................................... 558/86
[58] Field of Search ........................... 558/86; 435/198

[56] References Cited

U.S. PATENT DOCUMENTS 4,472,230  9/1984  Ashani et al. ........................ 558/86

OTHER PUBLICATIONS

*Biochimica et Biophysica Acta,* 711 (1982), 375–360.

*Primary Examiner*—Anton H. Sutto
*Attorney, Agent, or Firm*—George Tarnowski

[57] ABSTRACT

There are disclosed compounds of the formula $$R^1-X$$

wherein
  $R^1$ is alkyl of 8–22 carbon atoms;
  X is $$-NHC-O-R^2, -NHC-NH-R^2 \text{ or } -SO_2NH-R^2 \text{ and}$$
$$\phantom{-NH}\underset{O}{\|}\phantom{-O-R^2,\ -NH}\underset{O}{\|}$$

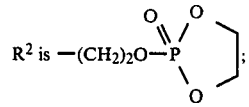

and their use in the prevention and/or treatment of conditions such as allergic rhinitis, allergic bronchial asthma and other naso-bronchial obstructive air-passageway conditions, other immediate hypersensitivity reactions such as allergic conjunctivitis and various inflammatory conditions.

4 Claims, No Drawings

2-[1,3,2-DIOXAPHOSPHOLAN-2-YLOXY]ETHYL COMPOUNDS

The present invention is directed to a series of substituted cyclic phoshotriesters having anti-inflammatory activity.

It is now well-established that arachidonic acid (AA) is metabolized in mammals by two distinct pathways. The metabolism of arachidonic acid by cyclooxygenase enzymes results in the production of prostaglandins and thromboxanes. The physiological activity of the prostaglandins arise from the endoperoxides $PGG_2$ and $PGH_2$ by the cyclooxygenase pathway of arachidonic acid metabolism. These endoperoxides are also the precursors of the thromboxanes (Tx) $A_2$ and $B_2$. $TxA_2$ is a vasoconstrictor which stimulates platelet aggregation. In the normal situation, the vasoconstrictive and platelet aggregating properties of the thromboxanes are balanced by another product arising from the endoperoxides in the cyclooxygenase pathway, prostacyclin ($PGI_2$), which is a vasodilator with platelet aggregation inhibitory activity. In the event prostacyclin synthesis is impaired and/or platelet activation is enhanced, then thrombosis and vasoconstriction is favored. The role of prostanoids in haemostasis and thrombosis are reviewed by R. J. Gryglewski, *CRC Crit. Rev. Biochem.*, 7, 291 (1980) and J. B. Smith, *Am. J. Pathol.*, 99, 743 (1980).

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., *J. Immun.* 215, 115–118 (1980); *Biochem. Biophys. Res. Commun.* 93, 1121–1126 (1980)].

The significance of these leukotrienes is that a great deal of evidence is accumulating showing that leukotrienes participate in inflammatory reactiions, exhibit chemotactic activities, stimulate lyosomal enzyme release and act as important factors in the immediate hypersensitivity reaction. It has been shown that $LTC_4$ and $LTD_4$ are potent bronchoconstrictors of the human bronchi [see Dahlen et al., *Nature* 288, 484–486 (1980)], and another leukiotriene, $LTB_4$, is a powerful chemotactic factor for leukocytes [see A. W. Ford-Hutchinson, *J. Roy. Soc. Med.*, 74, 831–833 (1981)]. The activity of leukotrienes and slow-reacting substances (SRS's) as mediators of inflammation and hypersensitivity is extensively reviewed in Bailey and Casey, *Ann. Reports Med. Chem.*, 17, 203–217 (1982).

It is now generally accepted that the release of free arachidonic acid from membrane phospholipids by the enzyme phospholipase $A_2$ ($PLA_2$) is the critical first step in the initiation of the synthesis of the various eicosanoids arising from the cyclooxygenase and lipoxygenase pathways. In this regard it may be noted that the anti-inflammatory steroids are thought to inhibit eicosanoid synthesis by inducing the synthesis of a $PLA_2$ inhibitory protein denominated macrocortin or lipomodulin [see Flower et al., *Nature, London*, 278, 456 (1979) and Hirata et al., *Proc. Natn. Acad. Sci. U.S.A.*, 77, 2533 (1980)]. $PLA_2$ catalyzes the specific hydrolysis of the fatty-acid ester linkage at the 2-position of 1,2-diacyl-sn-phosphoglycerides and two major pathways for the $PLA_2$-mediated arachidonic acid release have been proposed to account for phospholipid hydrolysis. According to the first, the $PLA_2$-mediated cleavage of AA from the 2-position of phosphatidylcholine and phosphatidylethanolamine occurs during platelet activation [Bills et al., *Biochem. Biophys. Acta*, 424, 303 (1976)], while according to the second, phosphatidylinositol, which turns over very rapidly, may also serve as the initial source of AA.

As the initial step leading to subsequent conversion of AA to the various eicosanoids by the cyclooxygenase and lipoxygenase pathways, the $PLA_2$-mediated release of AA from membrane phospholipids is a critical event in attempting to deal with the various physiological manifestations which are based on the activity of the prostaglandins, thromboxanes and leukotrienes. Thus, while $PLA_2$ has been shown to be required for platelet aggregation [Pickett et al., *Biochem. J.*, 160, 405 (1976)], cardiac contraction and excitation [Geisler et al., *Pharm. Res. Commun.*, 9, 117 (1977)], as well as prostaglandin synthesis [Vogt, *Adv. Prostagl. Thromb. Res.*, 3, 89 (1978)], the inhibition of $PLA_2$ is indicated in the therapeutic treatment if cyclooxygenase and/or lipoxygenase pathway product-mediated physiological conditions. Thus, $PLA_2$ inhibitors are a rational approach to the prevention, removal or amelioration of such conditions as allergy, anaphylaxis, asthma and inflammation.

The invention provides novel compounds of the formula $$R^1-X$$

wherein
$R^1$ is alkyl of 8–22 carbon atoms;
X is

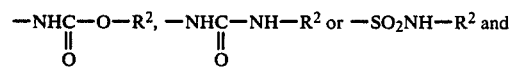

$R^2$ is 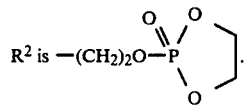

The compounds of the invention can be prepared by the following reaction schemes. The compounds of the formula

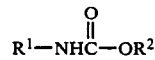

can be prepared by reacting the appropriate alkyl isocyanate with ethylene glycol:

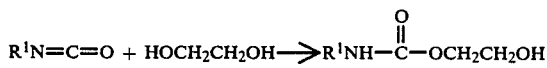

The reaction is preferably carried out in an organic solvent, such as tetrahydrofuran. The intermediate obtained thereby is then reacted with 2-chloro-2-oxo-1,3,2-dioxophospholane to yield the desired final product:

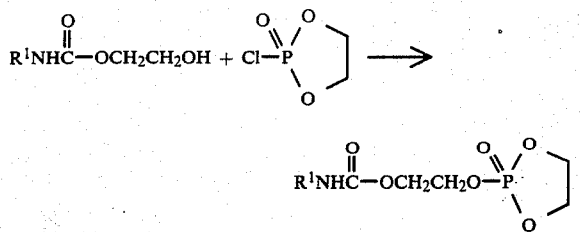

In like manner, when it is desired to obtain compounds having the formula

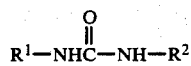

an appropriate alkyl isocyanate is reacted with ethanolamine:

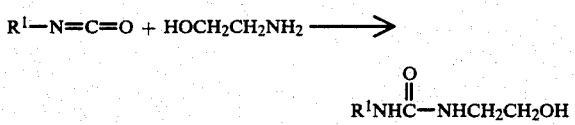

The reaction is carried out in an organic solvent, preferably tetrahydrofuran. The resulting intermediate is then reacted, as indicated above, with 2-chloro-2-oxo-1,3,2-dioxophospholane to yield the desired final product:

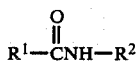

Finally, compounds of the invention having the formula

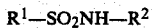

can be prepared by reacting the appropriate alkylsulfonyl halide with ethanolamine in an organic solvent, preferably tetrahydrofuran:

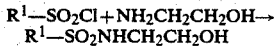

and then treated as described, supra, to obtain the desired final product.

All of the starting compounds of the invention are commercially available or can be readily prepared by conventional procedures taught in the chemical literature.

The compounds of the invention, by virtue of their ability to inhibit activity of $PLA_2$ enzyme, are useful in the treatment of conditions indicated by products of the oxidation of arachidonic acid. Accordingly, the compounds are indicated in the prevention and treatment of such conditions as allergic rhinitis, allergic bronchial asthma and other naso-bronchial obstructive air-passageway conditions, other immediate hypersensitivity reactions, such as allergic conjunctivitis; and various inflammatory conditions such as those present in rheumatoid arthritis, osteoarthritis, tendinitis, bursitis, psoriasis (and related skin inflammation) and the like.

When the compounds of the invention are employed in the treatment of allergic airways disorders or in anti-inflammatory therapy, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol. The compounds may also be used topically and for this purpose they may be formulated in the form of dusting powders, creams or lotions in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The standard pharmacological procedures, which are described fully in the examples given hereafter, illustrate the ability of the compounds of the invention to inhibit the activity of $PLA_2$ enzyme in vitro; and measures the in vivo activity of the compounds as anti-inflammatory agents in the murine assay.

EXAMPLE 1

N-[2-(1,3,2-Dioxaphospholan-2-yloxy)ethyl]-N'-dodecylurea P-oxide

A. N-hydroxyethyl-N'-dodecylurea 1.3 ml dodecyl isocyanate and 0.37 ml (6 mM) ethanolamine are combined at icebath temperature in 10 ml of tetrahydrofuran and stirred overnight at 4° C. and then evaporated under reduced pressure (<30° C.) to dryness. Ethyl acetate is added and the solid is triturated by magnetic stirring. The insoluble material is filtered, washed on the filter with ethyl acetate and dried in vacuo at room temperature to yield 1.3 gm of product.

Analysis for: $C_{15}H_{32}N_2O_2$. Calculated: C, 66.13; H, 11.84; N, 10.15. Found: C, 66.08; H, 11.59; N, 10.15.

IR KBr 1050, 1580–1620, 3410.

B. N-[2-(1,3,2-dioxaphospholan-2-yloxy)ethyl]-N'-dodecylurea P-oxide 545 mg (2 naeq) of A. above (241-1), 0.28 ml (2 naeq) of triethylamine and 0.29 ml of 2-chloro-2-oxo-1,3,2-dioxophospholane are combined in 15 ml benzene at icebath temperature and stirred overnight at 4° C. The reaction mixture is evaporated under reduced pressure (<30° C.) and dried in vacuo. The desired product is purified by chromatography on silica gel in the system methylene chloride:methanol (5:1). Chromatographic fractions 86–102 are combined (TLC silica gel methylene chloride:methanol (5:1) chlorine amide spray), evaporated under reduced pressure (<30° C.) and dried in vacuo to yield 250 mg of title product.

Analysis for: $C_{17}H_{35}N_2O_5P$. Calculated: C, 56.35; H, 9.70; N, 7.70. Found: C, 56.83; H, 10.32; N, 7.97.

IR KBr 1240, 1585, 1615, 2850, 2905.

EXAMPLE 2

Dodecylcarbamic acid 2-(1,3,2-dioxaphospholan-2-yloxy)ethyl ester P-oxide

A. Dodecylcarbamic acid, hydroxyethyl ester 4.2 ml dodecyl isocyanate and 2.4 ml of ethylene glycol are combined in tetrahydrofuran at room temperature and stirred overnight at room temperature. The resultant material is evaporated under reduced pressure (<30° C.), dried in vacuo, and purified by chromatography on a silica gel column using ethyl acetate as elutant. Fractions 74–94 are combined ($R_f$ 0.75 TLC Silica gel ethyl acetate iodine detection), evaporated under reduced pressure (<30° C.) and dried in vacuo to yield 546 mg of title product.

Analysis for: $C_{15}H_{31}NO_3$. Calculated: C, 66.89; H, 11.43; N, 5.12. Found: C, 66.17; H, 11.64; N, 5.51.

IR: 1675, 3300.

B. Dodecylcarbamic acid 2-(1,3,2-dioxaphospholan-2-yloxy)ethyl ester P-oxide 547 mg (2 meq.) of A. above, 0.28 ml (2 meq.) triethylamine and 0.29 ml of 2-chloro-2-oxo 1,3,2-dioxophospholane are combined in 15 ml of benzene at icebath temperature and stirred overnight at 4° C. The resultant material is evaporated under reduced pressure (<30° C.) and dried in vacuo. The crude product is purified by chromatography on silica gel with the system methylene chloride:methanol (10:1), fractions 66–68 being combined, evaporated under reduced pressure (<30° C.), and dried in vacuo.

Analysis for: $C_{17}H_{34}NO_6P$. Calculated: C, 53.8; H, 8.97; N, 3.7. Found: C, 53.05; H, 9.35; N, 3.82.

IR film: 1030, 1700, 1730(S), 2770, 2840, 3320.

EXAMPLE 3

N-[2-(1,3,2-dioxaphospholan-2-yloxy)ethyl]-1-hexadecanesulfonamide P-oxide

A. N-(Hydroxyethyl)-1-hexadecanesulfonamide 650 mg (2 meq.) of hexadecanesulfonyl chloride and 0.22 ml (2 meq.) of ethanolamine are combined in tetrahydrofuran at icebath temperature and stirred overnight at 4° C. The reaction mixture is evaporated under reduced pressure (<30° C.) and dried in vacuo. The product is purified by chromatography in the system methylene chloride:methanol (10:1) (silica gel).

Analysis for: $C_{18}H_{39}NO_3S$. Calculated: C, 61.90; H, 11.20; N, 4.0. Found: C, 61.86; H, 11.16; N, 4.40.

IR KBr 1130, 1470, 2860, 2920, 3300.

B. N-[2-(1,3,2-dioxaphospholan-2-yloxy)ethyl]-1-hexadecanesulfonamide P-oxide 349 mg (1 meq.) of A. above, 0.14 ml triethylamine and 0.15 ml of 2-chloro-2-oxo-1,3,2-dioxophospholane are combined at icebath temperature and stirred overnight at 4° C. The reaction mixture is evaporated under reduced pressure (<30° C.), dried in vacuo, and the product purified by silica gel chromatography in the system methylene chloride:methanol (10:1). Fractions 93–100 are combined, evaporated under reduced pressure (<30° C.) and dried in vacuo to yield 85 mg of the title compound.

Analysis for: $C_{20}H_{42}NO_6PS$. Calculated: C, 52.70; H, 9.20; N, 3.10. Found: C, 50.49; H, 9.32; N, 2.90.

IR KBr: 1060, 1470, 2860, 2920.

EXAMPLE 4

The ability of the compounds to inhibit the activity of $PLA_2$ enzyme is measured in the following in vitro assay.

The assay is carried out as follows:

Substrate Preparation

*E. coli*, cultured to exponential growth, are sedimented for 15 minutes at 10,000 g and resuspended in sterile isotonic saline (1–3 ml). 10–25 μCi [1-$^{14}$C] oleic acid (or arachidonic acid) is added to a sterile flask, evaporated by $N_2$ and resolubilized with 0.3 ml 20% fatty acid-free BSA. 75–100 ml of nutrient broth and 1 ml *E. coli* are then added to each flask and incubated for 2–3 hours at 37° C. [1-$^{14}$C] oleic acid labelled *E. coli* are then sedimented, suspended in saline and added to fresh nutrient broth and incubated for 1.5 hours at 37° C. to complete [1-$^{14}$C] oleic acid incorporation into the phospholipids. After overnight refrigeration of cultures, *E. coli* are again sedimented, suspended in saline and autoclaved for 15 minutes at 120° C. *E. coli* cultures are washed twice with saline (first wash contains 1% BSA) and resuspended in saline. Non-labelled *E. coli* cultures are also prepared in the same manner. Cell number is determined by measuring the optical density at 550 nm ($3 \times 10$ cell/ml=1 O.D.). The amount of radioactivity associated with cells is determined by counting a defined volume of cell suspension. The specific activity is subsequently adjusted by adding non-labelled *E. coli* to yield $2-4 \times 10$ cpm per $1 \times 10^{10}$ *E. coli*. [1-$^{14}$C] arachidonic acid-labelled *E. coli* are similarly prepared.

Platelet $PLA_2$ Preparation

Expired human platelets from the blood bank are centrifuged for 15 minutes at 200 g to obtain a platelet rich plasma fraction and to remove the red blood cells. Platelets are sedimented for 15 minutes at 2500 g and the plasma is removed before adding cold 0.18N $HSO_4$ (4 ml/unit). Platelets are homogenized, incubated for 1 hour at 4° C., homogenized again and centrifuged for 15 minutes at 10,000 g. The $PLA_2$ enriched supernatant fluid is removed and the amount of protein is determined by the Lowry method. The preparation is divided into various portions and stored at −20° C.

Assay of $PLA_2$ Activity

The assay measures the hydrolysis of *E. coli* membrane phospholipids and the release of free [1-$^{14}$C] oleic acid from the C-2 position of phospholipids by human platelet $PLA_2$. To ice cold $15 \times 100$ mm test tubes, the following additions are made: $2,5 \times 10$ *E. coli* (equivalent to 4 nmol phospholipid), 5 mM $Ca^{++}$, 100 mM Tris buffer (pH=7.4), 100 μg platelet extract (or an amount to produce 20–30% hydrolysis), drug or vehicle. The final volume is adjusted to 500 μl with water. Mixtures are vortexed and incubated for 30 minutes in a shaking bath. It should be noted that preliminary experiments are always performed with each new batch of platelets to establish linear hydrolysis of phospholipids with regard to protein concentration and time. The enzyme reaction is stopped by the addition of 3 volumes of $CHCl_3$ to each tube which is vortexed and then centrifuged for 5 minutes at 500 g. The lower CHCl$_3$/CH$_3$OH phase is removed and evaporated under N. The dried residue is redissolved in 50 μl CHCl$_3$:CH$_3$OH (9:1 v/v), spotted on aluminum-backed chromatographic plates and developed in a solvent system consisting of petroleum ether:diethyl ether:acetic acid (80:20:1). Free fatty acid ([1-$^{14}$C] oleic acid labeled phospholipids are visualized with exposure to iodine vapors. Radioactive areas that co-chromatographed with authentic oleic acid and phospholipid standards are cut out and placed in a scintillation vial. One ml CH$_3$OH and 10 ml Hydrofluor are added to each cut strip and radioactivity is determined by liquid scintillation counting.

The percent hydrolysis is calculated by the following equation:

$$\% \text{ Hydrolysis} = \frac{\text{free fatty acid(dpm)}}{\text{total phospholipid + free fatty acid(dpm)}}$$

Rate of Hydrolysis(nmol/min) =

$$\frac{\% \text{ hydrolysis} \times \text{total phospholipid content(5 nmol)}}{\text{incubation time(min)}}$$

Activity of standard drugs:

| Drug | Inhibition of PLA$_2$ Activity IC$_{50}$, μM |
|---|---|
| Indomethacin | 48 |
| Gold Sodium Thiomalate | 43 |

When tested in the above-described assay, the compounds of the invention gave the following results:

TABLE 1

| Compound of Example No. | % Inhibition of PLA$_2$ (at 100 μM) |
|---|---|
| 1 | 32 |
| 2 | 92 |
| 3 | 28 |

The results show the compounds of the invention to have PLA$_2$ inhibitory activity in the assay in question.

EXAMPLE 12

The ability of the compounds of the invention to inhibit the lipoxygenase and/or cyclooxygenase pathways of arachidonic acid is examined in the in vivo arachidonic acid (AA)-/12-O-tetradecanoylphorbol acetate (TPA)-induced murine ear edema test.

According to this test, Swiss Webster female mice (Buckshire), approximately 8 weeks old, are placed into plastic boxes in groups of six. Eight groups of mice receive AA topically on the right ear, and another 8 groups receive TPA topically on the right ear. AA and TPA are dissolved in acetone at concentrations of 100 mg/ml ad 100 μg/ml respectively. The phlogistics are applied to the right ear by the means of an automatic pipet. Volumes of 10 μl are applied to the inner and outer surfaces of the ear. Each mouse receives either 2 mg/ear AA or 4 μg/ear TPA. The left ear (control) receives acetone delivered in the same manner. Oral and topical dosing regimens are as follows: (1) drugs are given 30 minutes prior to AA treatment, and (2) drugs are given 30 minutes after treatment with TPA.

Measurements are taken with Oditest calipers, 0-10 mm with 0.01 graduations. The right and left ears are measured after 1 hour AA-induced inflammation and 4 hours after TPA-induced inflammation.

The difference between right and left ear thickness is calculated and the significance is determined by a one way analysis of variance with Dunnett's comparisons to control (P=0.05). Drug effects are expressed as a percent change from control values:

% change from control =

$$\frac{(\text{Rt. ear} - \text{Lt. ear})\text{drug} - (\text{Rt. ear} - \text{Lt. ear})\text{control}}{(\text{Rt. ear} - \text{Lt. ear})\text{control}} \times 100$$

The results for the compounds of the invention are presented in Table 2.

TABLE 2

| Compound of Example No. | Mouse Ear Edema Assay % Change from Control TOPICAL | |
|---|---|---|
| | AA[a] | TPA[a] |
| 2 | −16 | −38 |

[a] 1 mg/ear
[b] 100 mg/kg

The results show that the compound of the invention tested demonstrates topical activity against AA- and TPA-induced mouse ear edema, evidencing an inhibitory effect on acute skin inflammation mediated by products of the lipoxygenase and/or cyclooxygenase pathway.

What is claimed is:

1. A compound having the formula

R$^1$—X wherein
R$^1$ is alkyl of 8-22 carbon atoms;
X is

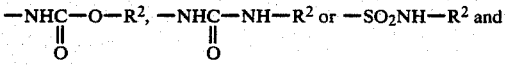

R$^2$ is 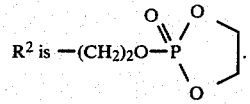

2. The compound of claim 1 having the name N-[2-(1,3,2-dioxaphospholan-2-yloxy)ethyl]-N'-dodecylurea P-oxide.

3. The compound of claim 1 having the name dodecylcarbamic acid 2-(1,3,2-dioxaphospholan-2-yloxy)ethyl ester P-oxide.

4. The compound of claim 1 having the name N-[2-(1,3,2-dioxaphospholan-2-yloxy)ethyl]-1-hexadecanesulfonamide P-oxide.

* * * * *